US010640473B2

(12) United States Patent
Gill et al.

(10) Patent No.: US 10,640,473 B2
(45) Date of Patent: May 5, 2020

(54) AZOLE DERIVATIVES FOR CORROSION MITIGATION

(71) Applicant: Ecolab USA Inc., St. Paul, MN (US)

(72) Inventors: Jasbir S. Gill, Naperville, IL (US); Shayan Moghadam, Naperville, IL (US); Thomas M. Miller, Aurora, IL (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/663,270

(22) Filed: Jul. 28, 2017

(65) Prior Publication Data

US 2018/0030000 A1 Feb. 1, 2018

Related U.S. Application Data

(60) Provisional application No. 62/368,546, filed on Jul. 29, 2016.

(51) Int. Cl.

| *C07D 249/18* | (2006.01) |
|---|---|
| *C23F 11/14* | (2006.01) |
| *C23F 11/10* | (2006.01) |
| *C01B 35/06* | (2006.01) |
| *C07C 275/00* | (2006.01) |
| *C08F 26/10* | (2006.01) |
| *C08L 33/26* | (2006.01) |

(52) U.S. Cl.

CPC ............ *C07D 249/18* (2013.01); *C23F 11/10* (2013.01); *C23F 11/149* (2013.01); *C01B 35/063* (2013.01); *C07C 275/00* (2013.01); *C08F 26/10* (2013.01); *C08L 33/26* (2013.01); *C09K 2208/32* (2013.01)

(58) Field of Classification Search
None
See application file for complete search history.

(56) References Cited

U.S. PATENT DOCUMENTS

| 3,985,503 | A | | 10/1976 | O'Neal, Jr. | |
|---|---|---|---|---|---|
| 4,206,075 | A | | 6/1980 | Boffardi | |
| 4,452,291 | A | | 6/1984 | Shemenski et al. | |
| 4,649,025 | A | * | 3/1987 | Hwa .................. | C23F 11/1676 252/180 |
| 5,330,683 | A | * | 7/1994 | Sufrin ...................... | C09K 5/20 252/387 |
| 5,411,677 | A | | 5/1995 | Pickering et al. | |
| 5,422,010 | A | | 6/1995 | Carey et al. | |
| 5,503,775 | A | * | 4/1996 | Rao ........................... | C02F 1/50 210/764 |
| 5,523,023 | A | | 6/1996 | Kleinstuck et al. | |
| 5,525,257 | A | | 6/1996 | Kleinstuck et al. | |
| 5,589,106 | A | | 12/1996 | Shim et al. | |
| 5,650,385 | A | | 7/1997 | Dunn et al. | |
| 5,736,495 | A | | 4/1998 | Bolkan et al. | |
| 5,772,919 | A | * | 6/1998 | Reichgott ............ | C07D 249/18 106/14.16 |
| 5,773,627 | A | | 6/1998 | Anderson et al. | |
| 5,874,026 | A | * | 2/1999 | Pilsits, Jr. ............. | C23F 11/149 252/394 |
| 5,911,906 | A | | 6/1999 | Miyake et al. | |
| 5,961,875 | A | | 10/1999 | Miyake et al. | |
| 6,096,236 | A | | 8/2000 | Miyake et al. | |
| 6,103,144 | A | * | 8/2000 | Cheng ................... | C23F 11/149 148/282 |
| 7,442,676 | B2 | | 10/2008 | Yang et al. | |
| 7,708,939 | B2 | * | 5/2010 | Duke ........................ | C02F 5/12 210/698 |
| 7,910,024 | B2 | * | 3/2011 | Stapp ...................... | C02F 1/683 106/14.12 |
| 8,012,374 | B2 | | 9/2011 | van Ooij et al. | |
| 8,236,205 | B1 | | 8/2012 | Matulewicz et al. | |
| 8,389,453 | B2 | * | 3/2013 | Thomson ............... | C11D 3/042 134/2 |
| 8,470,238 | B2 | * | 6/2013 | Sotoudeh ................ | C23F 14/02 106/14.16 |
| 8,658,326 | B2 | | 2/2014 | Marinho et al. | |
| 8,796,195 | B2 | * | 8/2014 | Thomson ............... | C11D 3/042 510/109 |
| 9,028,747 | B2 | | 5/2015 | Gill | |
| 9,222,174 | B2 | | 12/2015 | Gamer | |
| 2003/0035749 | A1 | | 2/2003 | Hann et al. | |
| 2006/0027782 | A1 | | 2/2006 | Wenderoth et al. | |
| 2008/0264870 | A1 | | 10/2008 | Duke et al. | |
| 2014/0119982 | A1 | | 5/2014 | Yang et al. | |

(Continued)

FOREIGN PATENT DOCUMENTS

| AU | 744545 B2 | 1/2000 |
|---|---|---|
| CA | 2116597 A1 | 10/1994 |
| CN | 101519513 A | 9/2009 |
| EP | 0971049 A1 | 1/2000 |
| JP | S57152476 A | 9/1982 |
| JP | S58130284 A | 8/1983 |
| JP | S59222589 A | 12/1984 |
| JP | S6018590 A | 1/1985 |
| JP | H04160173 A | 6/1992 |
| JP | H05230675 A | 9/1993 |
| KR | 1020090037142 A | 4/2009 |
| WO | 02/36503 A1 | 5/2002 |
| WO | 2017/031103 A1 | 2/2017 |

OTHER PUBLICATIONS

International Search Report and Written Opinion dated Nov. 3, 2017 relating to PCT Patent Application No. PCT/US2017/044469, 14 pages.

(Continued)

*Primary Examiner* — Joseph D Anthony
(74) *Attorney, Agent, or Firm* — Stinson LLP

(57) ABSTRACT

Anticorrosion compounds and compositions can be used in methods for preventing metal corrosion. More specifically, the method comprises contacting an anticorrosion composition to an aqueous system in contact with a metal. The anticorrosion composition comprises substituted and/or hydrogenated benzotriazoles and tolyltriazoles.

20 Claims, No Drawings

(56) References Cited

U.S. PATENT DOCUMENTS

| | | |
|---|---|---|
| 2015/0004054 A1 | 1/2015 | Richardson et al. |
| 2015/0045277 A1 | 2/2015 | Liu et al. |
| 2015/0118104 A1* | 4/2015 | Marin Cruz .......... C23F 11/149 422/7 |
| 2015/0159125 A1 | 6/2015 | Kneer |
| 2015/0284859 A1 | 10/2015 | Erickson et al. |
| 2016/0017200 A1 | 1/2016 | Yang et al. |

OTHER PUBLICATIONS

Li, Li et al., Preparation and characterization of pH-controlled-release intelligent corrosion inhibitor, Materials Letters, vol. 116, Feb. 2014, pp. 318-321.

Zin, I.M. et al., Corrosion Inhibition of Steel by Polycarboxylates, Materials Science, May 2015, vol. 50, Issue 6, pp. 903-907.

* cited by examiner

AZOLE DERIVATIVES FOR CORROSION MITIGATION

CROSS REFERENCE TO RELATED APPLICATIONS

This application claims priority to U.S. Provisional Patent Application Ser. No. 62/368,546 filed on Jul. 29, 2016, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Compounds and compositions are provided and can be used, for example, in methods for preventing metal corrosion. The methods comprise contacting an effective amount of an anticorrosion composition with an aqueous system in contact with a metal. The anticorrosion compositions comprise substituted and/or hydrogenated benzotriazoles and tolyltriazoles.

BACKGROUND OF THE INVENTION

Corrosion of metal surfaces in aqueous media has long been a problem for industries such as oil and gas, food and beverage, washing and sanitizing, pulp and paper, power generation, manufacturing, and utilities. For example, it is well known that during the production of oil and gas several corrosive components such as brines, organic acids, carbon dioxide, hydrogen sulfide, and microorganisms are present in various capacities. These harsh conditions can cause severe corrosion as evidenced by surface pitting, embrittlement, and general loss of metal. The metal surfaces can be composed of a high alloy steel including a chrome steel, a ferritic alloy steel, an austenitic stainless steel, a precipitation-hardened stainless steel, a high nickel content steel, copper, and a carbon steel.

In general, corrosion inhibitors protect the metal through formation of a passivation layer on the metal surface. This passivation layer wets the metal surface, which in turn prevents contact of the metal from the corrosive nature of the fluids. Typically, corrosion inhibitor formulations contain a variety of aliphatic organic surfactant molecules including amines, quaternary amines, imidazolines, phosphate esters, amides, carboxylic acids, or combinations thereof. However, in harsh environments (e.g., high salt and acidic pH) the formation of a passivation layer on the metal surface is decreased and the susceptibility of the metal surface to corrosion is increased.

Mitigation of corrosion and fouling is advantageous in all water based or aqueous systems. In the prior art, most of the additives that are commonly used for corrosion and fouling mitigation include phosphorus, such as orthophosphates, polyphosphates, or organic phosphates commonly known as phosphonates. While there has been some success attributed to phosphorus containing corrosion and fouling inhibitor compositions, it has recently been discovered that phosphorus is not environmentally friendly. As a result, environmental agencies have either mandated a reduction in its use or banned its use altogether.

Thus, there is a need to develop methods and chemistries to inhibit corrosion of metal surfaces exposed to harsh environments. Additionally, there is a need to develop methods and chemistries to inhibit corrosion of metal surfaces without the need of phosphorous or zinc.

SUMMARY OF THE INVENTION

Compounds are provided that can be used in methods for preventing metal corrosion. The method comprises contacting an effective amount of an anticorrosion composition with an aqueous system in contact with a metal. The anticorrosion composition can comprise an alkyl benzotriazole, an alkyl tolyltriazole, an alkoxy benzotriazole, an alkoxy tolyltriazole, a nitro benzotriazole, a nitro tolyltriazole, a halo benzotriazole, a halo tolyltriazole, a hydrogenated benzotriazole, a hydrogenated tolyltriazole an acid or a salt thereof, or a combination thereof. The aqueous system can comprise a brine and has an acidic pH.

Other objects and features will be in part apparent and in part pointed out hereinafter.

DESCRIPTION OF THE PREFERRED EMBODIMENTS

Due to the need to prevent metal corrosion in harsh environments, new anticorrosion compositions are needed that can form a passivation layer on a metal surface. The anticorrosion compositions of substituted and/or hydrogenated benzotriazoles and tolyltriazoles described herein can provide corrosion inhibition on metal surfaces in contact with aqueous environments that contain a high salt concentration (i.e., a brine) and have an acidic pH.

Compounds and compositions can be used in a method for preventing metal corrosion. The method comprises contacting an effective amount of an anticorrosion composition with an aqueous system being in contact with a metal. The anticorrosion composition comprises an alkyl benzotriazole, an alkyl tolyltriazole, an alkoxy benzotriazole, an alkoxy tolyltriazole, a nitro benzotriazole, a nitro tolyltriazole, a halo benzotriazole, a halo tolyltriazole, a hydrogenated benzotriazole, a hydrogenated tolyltriazole an acid or a salt thereof, or a combination thereof. The aqueous system can comprise a brine and has an acidic pH.

The anticorrosion composition does not contain phosphorus.

The alkyl benzotriazole can have from 1 to 6 alkyl substituents attached to a nitrogen atom of the azole or to a carbon atom of the aromatic ring and the alkyl substituents can be $C_1$ to $C_{12}$ alkyl groups.

Preferably, the alkyl benzotriazole can comprise butyl benzotriazole, pentyl benzotriazole, hexyl benzotriazole, heptyl benzotriazole, octyl benzotriazole, or a combination thereof.

The alkyl tolyltriazole can have from 1 to 5 alkyl substituents attached to a nitrogen atom of the azole or to a carbon atom of the aromatic ring and the alkyl substituents can be $C_1$ to $C_{12}$ alkyl groups.

Preferably, the alkyl tolyltriazole can comprise butyl tolyltriazole, pentyl tolyltriazole, hexyl tolyltriazole, heptyl tolyltriazole, octyl tolyltriazole, or a combination thereof.

Various alkyl benzotriazoles including butyl benzotriazole, hexyl benzotriazole, and heptyl benzotriazole are commercially available from Wincom Inc., Blue Ash, Ohio.

The alkoxy benzotriazole can have from 1 to 6 alkyl substituents attached to a nitrogen atoms of the azole or to a carbon atom of the aromatic ring and the alkyl substituents can be $C_1$ to $C_{12}$ alkyl groups.

Preferably, the alkoxy benzotriazole can comprise butoxy benzotriazole, pentoxy benzotriazole, hexoxy benzotriazole, heptoxy benzotriazole, octoxy benzotriazole, or a combination thereof.

The nitro benzotriazole can have the nitro group attached to one or more carbon atoms of the aromatic ring and can have a substituent of alkyl, alkoxy, or halo attached to a nitrogen atom of the azole or to a carbon atom of the aromatic ring.

Preferably, the nitro benzotriazole can comprise 3-nitrobenzotriazole, 4-nitrobenzotriazole, 5-nitrobenzotriazole, 6-nitrobenzotriazole, or a combination thereof.

Various nitro benzotriazoles can, for example, be prepared by reacting benzotriazole with nitric acid under various conditions including in the presence of sulfuric acid.

The halo benzotriazole can have the halo group attached to one or more carbon atoms of the aromatic ring and can have a substituent of alkyl, or alkoxy attached to a nitrogen atom of the azole or a substituent of alkyl, alkoxy, or nitro attached to a carbon atom of the aromatic ring.

Preferably, the halo benzotriazole can comprise 3-halo benzotriazole, 4-halo benzotriazole, 5-halo benzotriazole, 6-halo benzotriazole, or a combination thereof.

More preferably, the halo benzotriazole can comprise a fluoro benzotriazole, a chloro benzotriazole, a bromo benzotriazole, a iodo benzotriazole, or a combination thereof.

Various halo triazoles can be prepared by reacting benzotriazole or tolyl triazole with hypohalous acid and precipitating the halogenated product with a mineral acid.

The hydrogenated benzotriazole can have one or more additional hydrogen atoms added across one or more of the double bonds of the benzotriazole.

The hydrogenated tolyltriazole can have one or more additional hydrogen atoms added across one or more of the double bonds of the tolyltriazole.

Various hydrogenated triazoles including hydrogenated tolyltriazole are available under the Wintrol® trademark from Wincom Inc., Blue Ash, Ohio.

The aqueous system can have a conductivity of from about 1,000 to about 100,000 micromho/cm, from about 1,000 to about 80,000 micromho/cm, from about 1,000 to about 60,000 micromho/cm, from about 1,000 to about 50,000 micromho/cm, from about 1,000 to about 30,000 micromho/cm, from about 2,000 to about 100,000 micromho/cm, from about 2,000 to about 80,000 micromho/cm, from about 2,000 to about 60,000 micromho/cm, from about 2,000 to about 50,000 micromho/cm, from about 2,000 to about 30,000 micromho/cm, from about 5,000 to about 100,000 micromho/cm, from about 5,000 to about 80,000 micromho/cm, from about 5,000 to about 60,000 micromho/cm, from about 5,000 to about 50,000 micromho/cm, or from about 5,000 to about 30,000 micromho/cm.

The aqueous system can have a pH less than 5, less than 4.5, less than 4, less than 3.5, less than 3, less than 2.5, or less than 2.

Preferably, the aqueous system can have a pH less than 3.

More preferably, the aqueous system can have a pH less than 2.

The aqueous system can be further contacted with a salt of a nitrogen base having a fluoro inorganic anion.

The fluoro inorganic anion can comprise a borate anion.

Preferably, the fluoro inorganic anion can comprise tetrafluoroborate, hexafluorophosphate, or a combination thereof.

The nitrogen base can be urea, biuret, an alkyl urea, an alkanolamine, an alkylamine, a dialkylamine, a trialkylamine, an alkyldiamine, an alkyltriamine, an alkyltetramine, a polyamine, an acrylamide, a polyacrylamide, a vinyl pyrolidone, a polyvinyl pyrolidone, or a combination thereof.

Preferably, the nitrogen base can comprise urea.

The salt of a nitrogen base having a fluoro inorganic anion is disclosed in U.S. Pat. Nos. 8,389,453 and 8,796,195 and available commercially from Nalco-Champion as Product No. EC6697A.

The compositions can have the fluoro inorganic anion comprise tetrafluoroborate and the nitrogen base comprises urea and the molar ratio of urea to tetrafluroboric acid used to prepare the salt is 1:3 to 5:1, 1:3 to 4:1, 1:3 to 3:1, 1:2 to 5:1, 1:2 to 4:1, or 1:2 to 3:1. The nitrogen base (e.g., urea) can react with the fluoro inorganic acid (e.g., fluoroboric acid) to form the salt of a nitrogen base having a fluoro inorganic anion (e.g., urea tetrafluoroborate). However, the relative amounts and/or concentrations of the fluoro inorganic acid component and base component in the compositions can vary widely, depending on the desired function of the composition and/or the required cleaning activity. As such, the weight ratios and/or concentrations utilized can be selected to achieve a composition and/or system having the desired cleaning and health and safety characteristics.

The metal can comprise carbon steel.

The metal can be contained within a piece of equipment.

The piece of equipment can comprise a boiler, a steam generator, an evaporator, a heat exchanger, a cooling coil, a chiller, a tube bundle, a tank, a sump, a containment vessel, a pump, a distributor plate, a geothermal system, a production well, an injection well, a steam separator, a binary geothermal unit, a transfer pipe, an oil well, or a deep injection well.

Preferably, the piece of equipment using the methods described herein is an evaporator, a sugar production system, an ethanol production system, a steam generator, a thermal recovery system, or a water softening unit.

More preferably, the piece of equipment is part of a thermal recovery system, including a steam-assisted gravity drainage system or a cyclic steam stimulation system.

The aqueous system can be at a temperature from about 80° C. to about 500° C., from about 80° C. to about 450° C., from about 80° C. to about 400° C., from about 80° C. to about 350° C., from about 80° C. to about 300° C., from about 80° C. to about 250° C., from about 80° C. to about 200° C., from about 80° C. to about 150° C., from about 100° C. to about 500° C., from about 100° C. to about 450° C., from about 100° C. to about 400° C., from about 100° C. to about 350° C., from about 100° C. to about 300° C., from about 100° C. to about 250° C., from about 100° C. to about 200° C., from about 100° C. to about 150° C., from about 120° C. to about 500° C., from about 120° C. to about 450° C., from about 120° C. to about 400° C., from about 120° C. to about 350° C., from about 120° C. to about 300° C., from about 120° C. to about 250° C., from about 120° C. to about 200° C., from about 120° C. to about 150° C.

The aqueous system can have a temperature of from about 120° C. to about 300° C. and a pH of less than 2.

The anticorrosion composition can further optionally comprise a component of an additional corrosion inhibitor, an asphaltene inhibitor, a paraffin inhibitor, a scale inhibitor, a water clarifier, a dispersant, a gas hydrate inhibitor, a biocide, a pH modifier, a surfactant, or a combination thereof.

The component of the anticorrosion inhibitor can comprise an additional corrosion inhibitor. The anticorrosion composition can comprise from about 0.1 to 20 wt. %, 0.1 to 10 wt. %, or 0.1 to 5 wt. % of the an additional corrosion inhibitors, based on total weight of the Anticorrosion composition. An anticorrosion composition can comprise from 0.1 to 10 percent by weight of the an additional corrosion inhibitors, based on total weight of the composition. The anticorrosion composition can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt 13.5 wt %, 14.0 wt %, 14.5 wt %, or 15.0 wt % by weight of the an additional corrosion inhibitors, based on total weight of the Anticorrosion composition. Each system can have its own requirements, and the weight percent of one or more additional corrosion inhibitors in the composition can vary with the system in which it is used.

The additional corrosion inhibitor can comprise an imidazoline compound, a quaternary ammonium compound, a pyridinium compound, or a combination thereof.

The additional corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The additional corrosion inhibitor component can include an imidazoline of Formula (I):

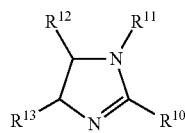

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The additional corrosion inhibitor component can include an imidazolinium compound of Formula (II):

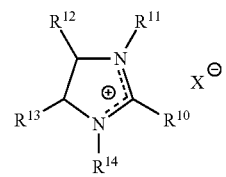

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2 hydroxyethyl)-2 tall-oil-2 imidazolinium chloride.

The additional corrosion inhibitor can comprise a bis-quaternized compound having the formula (III):

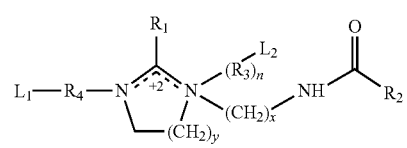

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; $R_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$ $C_{18}$ alkyl, $C_{16}$-$C_{18}$ alkyl, or a combination thereof; $R_3$ and $R_4$ are $C_1$-$C_{10}$ alkylene, $C_2$ $C_8$ alkylene, $C_2$ $C_6$ alkylene, or $C_2$ $C_3$ alkylene; n is 0 or 1; x is 2; y is 1; $R_3$ and $R_4$ are —C$_2$H$_2$; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$ $C_3$ alkylene such as —C$_2$H$_2$; n is 1 and $L_2$ is —COOH or n is 0 and $L_2$ is absent or H; x is 2; y is 1; $R_3$ and $R_4$ are —C$_2$H$_2$; and $L_1$ is —COOH.

It should be appreciated that the number of carbon atoms specified for each group of formula (III) refers to the main chain of carbon atoms and does not include carbon atoms that may be contributed by substituents.

The additional corrosion inhibitor can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$ $C_{18}$ alkyl, or $C_{16}$-$C_{18}$ alkyl or a combination thereof; $R_4$ is $C_1$-$C_{10}$ alkylene, $C_2$ $C_8$ alkylene, $C_2$ $C_6$ alkylene, or $C_2$ $C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R_4$ is —$C_2H_2$; x is 2; y is 1; n is 0; $L_1$ is —COOH, —SO$_3$H, or —PO$_3$H$_2$ and $L_2$ is absent or H.

The additional corrosion inhibitor can be a quaternary ammonium compound of Formula (IV):

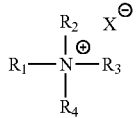

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each independently be alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethyl-aminoethanolamine quaternary ammonium salt.

additional

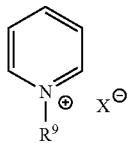

additional wherein R$^9$ is an alkyl group, an aryl group, or an arylalkyl group, wherein said alkyl groups have from 1 to about 18 carbon atoms and X$^-$ is a halide such as chloride, additional pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The additional corrosion inhibitor components can include additional corrosion inhibitors such as phosphate esters, monomeric or oligomeric fatty acids, or alkoxylated amines.

The additional corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2 hydroxyethyl groups, and hydroxylamine phosphate esters obtained by reacting polyphosphoric acid or phosphorus pentoxide with hydroxylamines such as diethanolamine or triethanolamine are preferred.

The additional corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The additional corrosion inhibitor component can comprise an alkoxylated amine. The alkoxylated amine can be an ethoxylated alkyl amine. The alkoxylated amine can be ethoxylated tallow amine.

The component of the anticorrosion composition can include an asphaltene inhibitor. The anticorrosion composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the anticorrosion composition can include an additional paraffin inhibitor. The anticorrosion composition can comprise from about 0.1 to 10 wt. %, from about 0.1 to 5 wt. %, or from about 0.5 to 4 wt. % of an additional paraffin inhibitor, based on total weight of the anticorrosion composition. Suitable additional paraffin inhibitors include, but are not limited to, paraffin crystal modifiers, and dispersant/crystal modifier combinations.

Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the anticorrosion composition can include a scale inhibitor. The anticorrosion composition can comprise from about 0.1 to 20 wt. %, from about 0.5 to 10 wt. %, or from about 1 to 10 wt. % of a scale inhibitor, based on total weight of the anticorrosion composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the anticorrosion composition can include a water clarifier. The anticorrosion composition can comprise from about 0.1 to 10 wt. %, from about 0.5 to 5 wt. %, or from about 0.5 to 4 wt. % of a water clarifier, based on total weight of the anticorrosion composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the anticorrosion composition can include a dispersant. The anticorrosion composition can comprise from about 0.1 to 10 wt. %, from about 0.5 to 5 wt. %, or from about 0.5 to 4 wt. % of a dispersant, based on total weight of the anticorrosion composition. Suitable dispersants include, but are not limited to, aliphatic phosphonic acids with 2 50 carbons, such as hydroxyethyl diphosphonic acid, and aminoalkyl phosphonic acids, e.g. polyaminomethylene phosphonates with 2 10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2 4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the anticorrosion composition can include a hydrogen sulfide scavenger. The anticorrosion composition can comprise from about 1 to 50 wt. %, from about 1 to 40 wt. %, or from about 1 to 30 wt. % of a hydrogen sulfide scavenger, based on total weight of the anticorrosion composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the anticorrosion composition can include a gas hydrate inhibitor. The anticorrosion composition can comprise from about 0.1 to 25 wt. %, from about 0.1 to 20 wt. %, or from about 0.3 to 20 wt. % of a gas hydrate inhibitor, based on total weight of the anticorrosion composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the anticorrosion composition can include a kinetic hydrate inhibitor. The anticorrosion composition can comprise from about 5 to 30 wt. %, from about 5 to 25 wt. %, or from about 10 to 25 wt. % of a kinetic hydrate inhibitor, based on total weight of the anticorrosion composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the anticorrosion composition can include a biocide. The anticorrosion composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2 bromo-2 nitropropane-3-diol (Bronopol) and 2 2 dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the anticorrosion composition can include a pH modifier. The anticorrosion composition can comprise from about 0.1 to 20 wt. %, from about 0.5 to 10 wt. %, or from about 0.5 to 5 wt. % of a pH modifier, based on total weight of the anticorrosion composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the anticorrosion composition can include a surfactant. The anticorrosion composition can comprise from about 0.1 to 10 wt. %, from about 0.5 to 5 wt. %, or from about 0.5 to 4 wt. % of a surfactant, based on total weight of the anticorrosion composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2 hydroxyethyl) amine oxides, alkyl amidopropyl dimethyl amine oxides, alkylamidopropyl-bis(2 hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Paraffin inhibitor compositions can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the anticorrosion composition may not contain any of the additional agents or additives.

Anticorrosion compositions can further include additional functional agents or additives that provide a beneficial property. The amount of an additional agent or additive, when present, will vary according to the particular composition being manufactured and its intended use as one skilled in the art will appreciate.

The compositions can be prepared by combining the components as described above.

The compositions can be used for reducing, inhibiting or preventing corrosion of a metal surface used in recovery, transportation, refining or storage of a hydrocarbon fluid containing elemental sulfur or polysulfide. The method comprises contacting any of the compositions described herein with the metal surface to reduce, inhibit or prevent corrosion of the metal surface.

The compositions can be used in any industry where it is desirable to inhibit corrosion from a metal surface which comes in contact with salt water or brine.

The compositions can be used in water systems, condensate, oil, and gas systems, or a combination thereof. The compositions can be applied to a gas or liquid produced, or used in the production, transportation, storage, refining or separation of crude oil or natural gas. The compositions can be applied to a gas stream used or produced in a coal-fired process, such as a coal-fired power plant.

Further, the compositions can be applied to a gas or liquid produced or used in a waste-water process, a farm, a slaughter house, a land-fill, a municipality waste-water plant, a coking coal process, or a biofuel process.

The compositions are useful for corrosion inhibition in a container, a processing facility, or a piece of equipment used in the food service or food processing industries. The compositions have particular value for use with food packaging materials and equipment, and especially for cold or hot aseptic packaging. Examples of process facilities in which the compositions can be employed include a milk line dairy, a continuous brewing system, a food processing line (e.g., a pumpable food system, a pumpable beverage line, a warewash machine, a low temperature warewash machine, dishware, a bottle washer, a bottle chiller, a warmer, a third sink washer), processing equipment (e.g., a tank, a vat, a line, a pump, a hose, or dairy processing equipment) The compositions can also be used in a transportation vehicle.

Additionally, the compositions can be used to inhibit corrosion in a tank, a line, a pump, or other equipment used for the manufacture and storage of soft drink materials, and in the bottling or a container for the beverages.

The compositions can also be used on or in other industrial equipment and in other industrial process streams such as a heater, a cooling tower, a boiler, a retort water, a rinse water, an aseptic packaging wash water, and the like.

Also, the compositions can be used to treat surfaces in recreational waters such as in a pool, a spa, a recreational flume, a water slide, a fountain, and the like.

The compositions can be used to inhibit the corrosion of a metal surface contacted with a cleaner for surfaces found in janitorial or housekeeping applications, food processing equipment, plant applications, or laundry applications. For example, the corrosion of washers, such as tunnel washers for washing textiles, may be inhibited according to methods disclosed herein.

The compositions can be used or applied in combination with a low temperature dish or warewash sanitizing final rinse, a toilet bowl cleaner, or a laundry bleach.

Definitions

Unless otherwise indicated, an alkyl group as described herein alone or as part of another group is an optionally substituted linear saturated monovalent hydrocarbon substituent containing from one to thirty carbon atoms and preferably one to thirty carbon atoms in the main chain, or one to twenty carbon atoms in the main chain, or an optionally substituted branched saturated monovalent hydrocarbon substituent containing three to thirty carbon atoms, and preferably three to twenty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "substituted" as in "substituted alkyl," and the like, means that in the group in question (i.e., the alkyl, alkenyl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, aryl, cycloalkyl, or heterocyclo), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The term "halo" or "halogen," as used herein, refers to a fluoro, chloro, bromo, or iodo radical.

The term "hydrogenated," as used herein, refers to the addition of one or more hydrogen atoms across one or more double bonds.

The term "phosphorus" is intended to include not only phosphorus, but also phosphorus bearing additives, phosphorus derivatives, etc. In other aspects, the compositions do not include any phosphorus.

Having described the invention in detail, it will be apparent that modifications and variations are possible without departing from the scope of the invention defined in the appended claims.

EXAMPLES

The following non-limiting examples are provided to further illustrate the present invention.

Example 1: Weight Loss Tests

An aliquot (400 mL) of 15 wt. % of a fluoro inorganic anion (commercially available from Nalco Champion as Product No. EC6697A) was placed in a 600 mL glass lined Parr reactor. A corrosion inhibitor, butyl benzotriazole, chlorinated tolyl triazole, or a blend of butyl benzotriazole, hydrogenated tolyl triazole and benzotriazole was added in varying amounts to Parr reactor, see Table 1. To simulate underground conditions, 120 mg/L of calcium as calcium ions (and chloride counterions) and 2000 mg/L of chloride as chloride ions (with sodium counterions) were added. Two pre-weighted mild steel coupons approximately 75×13×1.5 mm were suspended in the fluid. The reactor was closed and the headspace was purged gently with nitrogen for five minutes. The reactor was heated to 130° C. for 47 hours then cooled to room temperature. Once the reactor returned to room temperature, the mild steel coupons were removed, rinsed with deionized water, and weighed. The weight loss was calculated by subtracting the final weight from the pre-weight.

The corrosion rate was determined using the following equation:

Corrosion Rate=$(K \cdot W)/(A \cdot T \cdot D)$ wherein K is a constant ($3.45 \times 10^6$ mils·hr·cm$^{-1}$·yr$^{-1}$); W is mass loss in grams; A is area in cm$^2$; and T is exposure time in hours; and D is density in g/cm$^3$.

The results of the weight loss tests are listed in Table 1.

TABLE 1

| Corrosion inhibition using butyl benzotriazole | |
|---|---|
| Inhibitor Concentration (ppm) | Corrosion rate MPY (mils per year) |
| 0 | 37 |
| 10 | 24 |

TABLE 1-continued

| Corrosion inhibition using butyl benzotriazole | |
|---|---|
| Inhibitor Concentration (ppm) | Corrosion rate MPY (mils per year) |
| 50 | 13 |
| 100 | 7.8 |
| 200 | 5.4 |

Example 2: Corrosion Tests

Corrosion tests were performed using a potentiostat (Gamry Instruments, Warminster, Pa.) equipped with a carbon steel (C1010) electrode with dimensions 1.27 cm (0.5 in) long and 1.27 cm (0.5 in) outer diameter (5 cm$^2$). The electrode was assembled on a PINE rotator and immersed in water. The rotator was rotated at 600 rpm to simulate a flow rate of 3-5 feet per second. The potentiostat connected to the rotator is capable of changing the potential of the metal in a controlled setting and measures the current as a function of applied potential. The test was performed for 48 hours.

The electrode was polarized at ±10 mV during these tests. The polarization was relative to the potential measured when there was no current flowing through the specimen which is called the Open Circuit Potential (OCP).

As the potential of the carbon steel electrode changed, a current was induced to flow between the working electrode (carbon steel) and counter electrodes. The carbon steel's resistance to polarization was found by taking the slope of the potential versus current curve. This resistance was then used to find the corrosion rate of the material using the Stern-Geary equation.

Agents including halogenated tolyltriazole, halogenated benzotriazole, butyl benzotriazole, hydrogenated triazole, and blends thereof can undergo similar corrosion tests. In some cases a blend of dispersants including polymaleic acid and a copolymer of acrylic acid and acrylamide t-butyl sulfonic acid (ATBS) were dosed into a synthetic water with composition in Table 2, at either 11 ppm or 22 ppm. The standard 13 water was prepare by combining 208.5 g $CaCl_2 \cdot 2H_2O$, 174.8 g $MgSO_4 \cdot 7H_2O$, 174.9 g $NaHCO_3$, and 400 ppm of chloride ion from NaCl in 250 gallons of water.

TABLE 2

| Water Composition | |
|---|---|
| Water Element | Concentration as mg/L |
| pH | 8.33 |
| Conductivity | 750 µS/Cm |
| Calcium* | 150 |
| Magnesium* | 75 |
| M - Alkalinity | 120 |
| Chloride | 130 |
| Sulfate | 75 |

*as calcium carbonate

Corrosions test were performed at 50° C. in standard 13 water. Additionally, 400 ppm Cl as NaCl was added to make the water more corrosive than standard 13 water.

TABLE 3

| Corrosion Study using Halogenated Tolytriazole and 3DT138 | | |
|---|---|---|
| Inhibitor | Dosage | MPY |
| halogenated tolyltriazole | ~11 ppm | 1.31 |

TABLE 3-continued

Corrosion Study using Halogenated Tolytriazole and 3DT138

| Inhibitor | Dosage | MPY |
| --- | --- | --- |
| halogenated tolyltriazole | ~22 ppm | 1.46 |
| halogenated tolyltriazole + dispersants | ~11 ppm (each) | 1.07 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method for preventing metal corrosion, the method comprising contacting an effective amount of an anticorrosion composition with an aqueous system in contact with a metal, the anticorrosion composition comprising an alkyl benzotriazole, an alkyl tolyltriazole, an alkoxy benzotriazole, an alkoxy tolyltriazole, a nitro benzotriazole, a nitro tolyltriazole, a halo benzotriazole, a halo tolyltriazole, a hydrogenated benzotriazole, a hydrogenated tolyltriazole, an acid or a salt thereof, or a combination thereof; wherein the aqueous system comprises a brine and has a pH less than 3 and the alkyl benzotriazole is butyl benzotriazole, pentyl benzotriazole, hexyl benzotriazole, heptyl benzotriazole, octyl benzotriazole, or a combination thereof.

2. The method of claim 1, wherein the anticorrosion composition does not contain phosphorous.

3. The method of claim 1, wherein the alkyl tolyltriazole is butyl tolyltriazole, pentyl tolyltriazole, hexyl tolyltriazole, heptyl tolyltriazole, octyl tolyltriazole, or a combination thereof; the alkoxy benzotriazole is butoxy benzotriazole, pentoxy benzotriazole, hexoxy benzotriazole, heptoxy benzotriazole, octoxy benzotriazole, or a combination thereof; the nitro benzotriazole is 3-nitrobenzotriazole, 4-nitrobenzotriazole, 5-nitrobenzotriazole, 6-nitrobenzotriazole, or a combination thereof; and the halo benzotriazole is a fluoro benzotriazole, a chloro benzotriazole, a bromo benzotriazole, an iodo benzotriazole, or a combination thereof.

4. The method of claim 1, wherein the alkyl tolyltriazole has from 1 to 5 alkyl substituents attached to a nitrogen atom of the azole or to a carbon atom of the aromatic ring and the alkyl substituents are $C_1$ to $C_{12}$ alkyl groups.

5. The method of claim 1, wherein the alkoxy benzotriazole has from 1 to 6 alkyl substituents attached to a nitrogen atoms of the azole or to a carbon atom of the aromatic ring and the alkyl substituents are $C_1$ to $C_{12}$ alkyl groups.

6. The method of claim 1, wherein the nitro benzotriazole has the nitro group attached to one or more carbon atoms of the aromatic ring and has a substituent of alkyl, alkoxy, or halo attached to a nitrogen atom of the azole or to a carbon atom of the aromatic ring.

7. The method of claim 1, wherein the halo benzotriazole has the halo group attached to one or more carbon atoms of the aromatic ring and has a substituent of alkyl or alkoxy attached to a nitrogen atom of the azole or a substituent of alkyl, alkoxy, or nitro attached to a carbon atom of the aromatic ring.

8. The method of claim 7, wherein the halo benzotriazole is 3-halo benzotriazole, 4-halo benzotriazole, 5-halo benzotriazole, 6-halo benzotriazole, or a combination thereof.

9. The method of claim 1, wherein the hydrogenated benzotriazole has one or more additional hydrogen atoms added across one or more of the double bonds of the benzotriazole and the hydrogenated tolyltriazole has one or more additional hydrogen atoms added across one or more of the double bonds of the tolyltriazole.

10. The method of claim 1, wherein the aqueous system has a conductivity of from about 2,000 to about 100,000 micromho/cm.

11. A method for preventing metal corrosion, the method comprising contacting an effective amount of an anticorrosion composition with an aqueous system in contact with a metal, the anticorrosion composition comprising an alkyl benzotriazole, an alkyl tolyltriazole, an alkoxy benzotriazole, an alkoxy tolyltriazole, a nitro benzotriazole, a nitro tolyltriazole, a halo benzotriazole, a halo tolyltriazole, a hydrogenated benzotriazole, a hydrogenated tolyltriazole, an acid or a salt thereof, or a combination thereof; wherein the aqueous system comprises a brine and has a pH less than 3 and is further contacted with a salt of a nitrogen base having a fluoro inorganic anion.

12. The method of claim 11, wherein the aqueous system has a pH of less than 2.

13. The method of claim 11, wherein the aqueous system has a temperature of from about 80° C. to about 400° C.

14. The method of claim 13, wherein the aqueous system has a temperature of from about 120° C. to about 300° C.

15. The method of claim 11, wherein the nitrogen base is urea, biuret, an alkyl urea, an alkanolamine, an alkylamine, a dialkylamine, a trialkylamine, an alkyldiamine, an alkyltriamine, an alkyltetramine, a polyamine, an acrylamide, a polyacrylamide, a vinyl pyrolidone, a polyvinyl pyrolidone, or a combination thereof.

16. The method of claim 11, wherein the fluoro inorganic anion comprises tetrafluoroborate and the nitrogen base comprises urea and the molar ratio of urea to tetrafluroboric acid used to prepare the salt is 1:3 to 3:1.

17. The method of claim 1, wherein the metal comprises carbon steel.

18. The method of claim 1, wherein the metal is contained within a piece of equipment and the piece of equipment is a boiler, a steam generator, an evaporator, a heat exchanger, a cooling coil, a chiller, a tube bundle, a tank, a sump, a containment vessel, a pump, a distributor plate, a geothermal system, a production well, an injection well, a steam separator, a binary geothermal unit, a transfer pipe, an oil well, or a deep injection well.

19. The method of claim 11, wherein the metal comprises carbon steel.

20. The method of claim 11, wherein the metal is contained within a piece of equipment and the piece of equipment is a boiler, a steam generator, an evaporator, a heat exchanger, a cooling coil, a chiller, a tube bundle, a tank, a sump, a containment vessel, a pump, a distributor plate, a geothermal system, a production well, an injection well, a steam separator, a binary geothermal unit, a transfer pipe, an oil well, or a deep injection well.

\* \* \* \* \*

UNITED STATES PATENT AND TRADEMARK OFFICE
CERTIFICATE OF CORRECTION

PATENT NO. : 10,640,473 B2
APPLICATION NO. : 15/663270
DATED : May 5, 2020
INVENTOR(S) : Jasbir S. Gill et al.

Page 1 of 1

It is certified that error appears in the above-identified patent and that said Letters Patent is hereby corrected as shown below:

In the Claims

Column 16, Claim 16, Line 47: "tetrafluroboric"
Should read -- tetrafluoroboric --

Signed and Sealed this
Twenty-fifth Day of April, 2023

Katherine Kelly Vidal
*Director of the United States Patent and Trademark Office*